United States Patent [19]

Sargent

[11] Patent Number: 4,935,524

[45] Date of Patent: Jun. 19, 1990

[54] FLUORINATED POLYCYCLIC COMPOUNDS

[75] Inventor: Colin R. Sargent, Bristol, Great Britain

[73] Assignee: ISC Chemicals Limited, London, England

[21] Appl. No.: 430,438

[22] Filed: Nov. 2, 1989

[30] Foreign Application Priority Data

Nov. 4, 1988 [GB] United Kingdom ............... 8825846

[51] Int. Cl.$^5$ ........................................... C07D 209/82
[52] U.S. Cl. .................................................. 548/439
[58] Field of Search ....................................... 548/439

[56] References Cited

PUBLICATIONS

Petrova et al., *Chemical Abstracts*, vol. 68 (1968), No. 49394z.

*Primary Examiner*—Robert W. Ramsuer

*Attorney, Agent, or Firm*—Fleit, Jacobson, Cohn, Price, Holman & Stern

[57] ABSTRACT

A fully fluorinated and fully-saturated heterocyclic organic compound of general formula

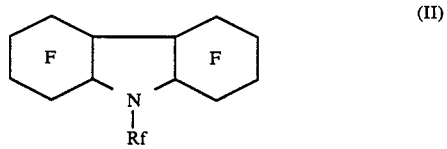

(II)

wherein the saturated rings F are fully fluorinated, and where the Rf radical is selected from perfluoro-alkyl groups, perfluoro-alicyclic groups, and mixed perfluoro-cycloalkyl-alkyl groups, and wherein the Rf radical contains from 1 to 10 carbon atoms inclusive. The compounds are high temperature heat transfer fluids.

8 Claims, No Drawings

FLUORINATED POLYCYCLIC COMPOUNDS

This invention relates to fluorinated polycyclic compounds, in particular perfluorinated polycyclic compounds containing at least one hetero-atom in at least one ring.

Very little success has been reported, in the chemical literature, on the subject of total fluorination of nitrogen-containing compounds with higher metal fluorides.

However, UK patent no. GB-2,113,223B describes a process wherein quinoline is heated with cobaltic fluoride at 250°–400° C. Unfortunately, the product is not a saturated perfluoroperhydro-quinoline, but rearrangement occurs giving perfluoro-1-azabicyclo-(5,3,0) decane. This work is reported in J. Fluorine Chemistry, 1982, 21, 413.

There is a need for a high temperature heat-transfer fluid which boils in the range 200°–350° C., especially in the context of condensation re-flow soldering (see for example "Tin and Its Uses" No. 130 (1981) pages 1–3; and "Electronic Production", June 1980 pages 21–27) which requires the latent heat of the fluid to melt the solder by using the latent heat of a vapour to produce a soldered joint.

We have now discovered that a range of heat-stable and high boiling heat-transfer fluids can be synthesised without gross degradation by the saturation fluorination of N-substituted carbazoles of the general formula

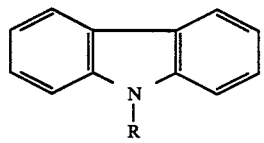

(I)

where R is an alkyl group having 1–10 carbon atoms (inclusive), an aromatic group or an alicyclic group, or an aralkyl group, e.g. benzyl.

The products are inert liquids which boil in the range 200°–350° C. and are thermally very stable; this makes them ideal for the proposed use.

The present invention provides heat-stable heterocyclic compounds of the general formula

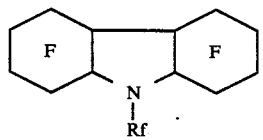

(II)

where the rings F are fully fluorinated (and saturated), and where Rf is a perfluoro-alkyl group or a perfluoro-alicyclic group, e.g. perfluoro-cyclo-hexyl, or a mixed perfluoro-cycloalkyl-alkyl group, e.g. perfluoro-cyclo-hexylmethyl, providing that Rf has 1–10 carbon atoms.

Preferably the product is a liquid boiling in the range 200° to 350° C.

The invention in another aspect provides a process for the preparation of a compound according to the first aspect of the invention, wherein the corresponding hydrocarbon N-substituted carbazole is fluorinated over a higher metal fluoride at 300°–500° C.

The higher metal fluoride is preferably cobaltic fluoride.

As fluorinating agents there may be used any of the higher metal fluorides which are capable of donating at least one fluorine atom to the organic compound while themselves being reduced to a lower valency state. Typical examples are cobaltic fluoride, $CoF_3$, and potassium cobaltic fluoride, $KCoF_4$. These should preferably be employed in finely-divided form as powders or granules and at a temperature within the range 300°–450° C.

The invention will now be further described with reference to the following non-limiting Examples 1–6, which describe the saturation fluorination of N-substituted carbazoles.

EXAMPLE 1

Perfluoro-perhydro-N-ethyl-carbazole

N-ethyl-carbazole (200 g) was fluorinated in four portions of 50 g each at 450° C. in a paddle-stirred horizontal reactor containing cobaltic fluoride powder (about 10 Kg) to give a crude product (346 g.).

Analysis by g.l.c. and g.l.c/m.s. (gas liquid chromatography/mass spectroscopy) showed the product to contain a total of 65% of a group resolved into four components, each showing a top mass of either 657($C_{14}F_{25}N$), the parent ion of perfluoro-8-aza-8-ethyl[7,4,0,0$^{2,7}$]tridecane (II; Rf=$C_2F_5$) or 638 (P-F).

After a work-up which included fractional distillation and chemical purification stages, to remove unsaturated and hydrogen-containing impurities, a perfluorinated fluid was obtained which boiled at 216°–220° C.

EXAMPLE 2

Perfluoro-perhydro-N-methyl-carbazole

N-Methyl-carbazole was fluorinated over cobaltic fluoride at 445° as described in Example 1, and the crude product was washed and filtered. Analysis by gas chromatography-linked mass spectroscopy showed this product to contain 36% of compounds with the target perfluorinated formula, ($C_{13}F_{23}N$, M.Wt. 607), as a mixture of stereo isomers. Structures were deduced from the molecular weights and the synthetic route.

On working up in the manner described in Example 1, a substantially pure sample of perfluoro-perhydro-N-methyl carbazole was obtained, which boiled in the range 203°–206° C.

EXAMPLE 3

Perfluoro-perhydro-N-(n-propyl)-carbazole

N-(n-propyl)-carbazole was fluorinated over cobaltic fluoride at 445° C. as described in Example 1, and the crude product was washed and filtered. Analysis by gas chromatography-linked mass spectroscopy showed this product to contain 59% of a compound with the target perfluorinated formula, ($C_{15}F_{27}N$, M.Wt. 707), as a mixture of stereo isomers. Structures were deduced from the molecular weights and the synthetic route.

On working up in the manner described in Example 1, a substantially pure sample of perfluoro-perhydro-N-(n-propyl)-carbazole was obtained, which boiled in the range 230°–235° C.

EXAMPLE 4

Perfluoro-perhydro-N-(n-pentyl)-carbazole

N-(n-pentyl)-carbazole was fluorinated over cobaltic fluoride at 450° C. as described in Example 1, and the crude product was washed and filtered. Analysis by gas chromatography-linked mass spectroscopy showed this product to contain 33% of a compound with the target perfluorinated formula, ($C_{17}F_{31}N$, M.Wt. 807), as a mixture of stereo isomers. Structures were deduced from the molecular weights and the synthetic route.

On working up in the manner described in Example 1, a substantially pure sample of perfluoro-perhydro-N-(n-pentyl)-carbazole was obtained, which boiled in the range 250°–260° C.

EXAMPLE 5

Perfluoro-perhydro-N-benzyl-carbazole

N-benzyl-carbazole was fluorinated over cobaltic fluoride at 450° C. as described in Example 1, and the crude product was washed and filtered.

Analysis by gas chromatography-linked mass spectroscopy showed the product to contain 21% of a compound with the target perfluorinated formula perfluoro-8-aza-8-cyclohexylmethyl[7,4,0,0$^{2,7}$]tridecane, ($C_{19}F_{33}N$, M.Wt. 869), (by assessment of the fragmentation pattern in the mass spectrum) as a mixture of stereo isomers. Structures were deduced from the molecular weights and the synthetic route.

The compound obtained, perfluoro-perhydro-N-benzyl-carbazole, is a fully fluorinated and fully saturated compound, the term 'benzyl' in the nomenclature thereof referring to the benzyl substituent of the starting material from which the compound is obtained.

EXAMPLE 6

Perfluoro-perhydro-N-(n-nonyl)-carbazole

N-(n-nonyl)-carbazole was fluorinated over cobaltic fluoride at 450° C. as described in Example 1, and the crude product was washed and filtered. Analysis by gas chromatography-linked mass spectroscopy showed the product to contain 29% of a compound with the target perfluorinated formula perfluoro-8-aza-8-nonyl-[7,4,0,0$^{2,7}$]tridecane, ($C_{21}F_{39}N$ (M.Wt 1007), (by assessment of the fragmentation pattern in the mass spectrum) as a mixture of stereo isomers. Structures were deduced from the molecular weights and the synthetic route.

I claim:

1. A fully fluorinated and fully-saturated heterocyclic organic compound of general formula

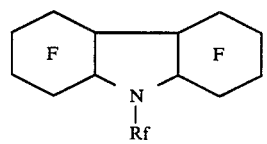

(II)

wherein the saturated rings F are fully fluorinated, and where the Rf radical is selected from the group consisting of perfluoro-alkyl groups, perfluoro-alicyclic groups, and mixed perfluoro-cycloalkyl-alkyl groups, and wherein the Rf radical contains from 1 to 10 carbon atoms inclusive.

2. Perfluoro-perhydro-N-ethyl-carbazole.
3. Perfluoro-perhydro-N-methyl-carbazole.
4. Perfluoro-perhydro-N-(n-propyl)-carbazole.
5. Perfluoro-perhydro-N-(n-pentyl)-carbazole.
6. Perfluoro-perhydro-N-benzyl-carbazole.
7. Perfluoro-perhydro-N-(n-nonyl)-carbazole.
8. The compound according to claim 1, wherein the product is a liquid boiling at from 200° to 350° C.

* * * * *